United States Patent [19]
Dias

[11] Patent Number: 5,515,850
[45] Date of Patent: May 14, 1996

[54] APPARATUS FOR COUPLING ACOUSTIC WAVES WITH AN ACOUSTIC WAVEGUIDE

[75] Inventor: J. Fleming Dias, Palo Alto, Calif.

[73] Assignee: Hewlett-Packard Company, Palo Alto, Calif.

[21] Appl. No.: 330,032

[22] Filed: Oct. 27, 1994

Related U.S. Application Data

[63] Continuation-in-part of Ser. No. 72,828, Jun. 7, 1993, Pat. No. 5,400,788.

[51] Int. Cl.$^6$ ..................................................... A61B 8/00
[52] U.S. Cl. .............................. 128/662.03; 128/662.06
[58] Field of Search ....................... 128/662.03, 662.06; 333/147, 149; 385/7, 123; 604/101

[56] References Cited

U.S. PATENT DOCUMENTS

| | | | |
|---|---|---|---|
| 4,445,892 | 5/1984 | Hussein et al. | 604/101 |
| 5,029,588 | 7/1991 | Yock et al. | 128/662.06 |
| 5,254,112 | 10/1993 | Sinofsky et al. | 128/662.06 X |
| 5,371,483 | 12/1994 | Bhardwaj | 128/662.06 X |
| 5,400,788 | 3/1995 | Dias et al. | 128/662.06 |

*Primary Examiner*—Francis Jaworski
*Attorney, Agent, or Firm*—Jack Lenell

[57] ABSTRACT

An apparatus for providing efficient transmission of a beam of acoustic wave between an ultrasonic transducer and a remotely located body under examination by the beam. The apparatus includes a housing having an interior arranged so that the ultrasonic transducer is disposed therein. A prism is acoustically coupled with the transducer and with an acoustic waveguide having a longitudinal dimension extending outwardly from the interior of the housing. The acoustic prism is fixedly coupled with a proximate portion of the waveguide so as to provide efficient transmission of the beam of acoustic waves between the prism and the waveguide. Accordingly, The beam of acoustic waves is transmitted from the transducer, through the prism, and along the longitudinal dimension of the waveguide, to a distal portion of the waveguide. The distal portion of the waveguide is inserted into a remotely located patient's body under examination. The distal portion of the waveguide emits the ultrasonic beam, scanning the tissue of interest.

12 Claims, 3 Drawing Sheets

APPARATUS FOR COUPLING ACOUSTIC WAVES WITH AN ACOUSTIC WAVEGUIDE

CROSS-REFERENCE TO RELATED APPLICATIONS

This is a continuation in part of a application, serial number 08/072828, filed on Jun. 7, 1993 now U.S. Pat. No. 5,400,788, by Dias et al. entitled "An Apparatus That Generates Acoustic Signals At Discrete Multiple Frequencies And That Couples Acoustic Signals Into A Cladded-Core Acoustic Waveguide".

FIELD OF THE INVENTION

The invention relates generally to the field of ultrasonic diagnostic probes and more particularly relates to the field of invasive ultrasound diagnostic probes.

BACKGROUND OF THE INVENTION

Ultrasonic probes provide a convenient and accurate way of gathering information about various structures of interest within a body being analyzed. In general, the various structures of interest have acoustic impedances that are different from the acoustic impedance of a medium of the body surrounding the structures. In operation, such ultrasonic probes generate acoustic waves that are acoustically coupled from the probe into the medium of the body, so that the acoustic waves are transmitted into the body.

For example, medical ultrasonic probes provide a convenient and accurate way for a physician to collect imaging data of various anatomical parts, such as heart tissue or fetal tissue structures within a body of a patient. In general, the heart or fetal tissues of interest have acoustic impedances that are different than an acoustic impedance of bodily fluids surrounding the tissue structures.

In some previously known invasive probes, such as some previously known catheter-type probes capable of imaging inside of a blood vessel or artery, acoustic coupling is achieved by inserting a portion of the probe into the patient's body and through an incision of the blood vessel or artery. For example the probe includes a probe housing, which is inserted into the patients body. The probe housing contains an piezoelectric transducer that generates a beam of ultrasonic acoustic waves. The beam is transmitted through a wall of the probe housing and scans the interior of the blood vessel.

As the acoustic waves propagate through the body, a portion of the acoustic waves are weakly reflected by the various structures within the body, transmitted through the wall of the housing, and received by the transducer. As the weakly reflected acoustic waves propagate through the transducer, they are electrically sensed by electrodes coupled thereto. By analyzing a relative temporal delay and intensity of the weakly reflected waves received by the transducer, imaging system components that are electrically coupled to the electrodes construct an image from the weakly reflected waves to illustrate spaced relation of the various tissue structures within the patient's body and qualities related to the acoustic impedance of the tissue structures. The physician views the reconstructed image on a display device coupled to the imaging system.

Since the acoustic waves are only weakly reflected by the tissue structures of interest, it is important to try to provide efficient acoustic transmission between the transducer and the body under examination. Such efficient acoustic transmission would insure that strength of the acoustic waves generated by the transducer is not excessively diminished as the waves are transmitted from the transducer into the medium of the body. Additionally, such efficient acoustic transmission would insure that strength of the weakly reflected waves are not excessively diminished as the reflected waves are received by the transducer from the medium of the body.

Furthermore, it is undesirable to insert the transducer into the patients body because the piezoelectric transducer may emit leakage currents inside the body, which could possibly induce life threatening fibrillation when the probe images a coronary artery. Furthermore, extended lengths of wires coupled to the electrodes of the inserted transducer act as antennas, which may receive undesirable radio frequency interference signals that could obscure electrical signals representative of an acoustic image.

What is needed is an apparatus that provides efficient coupling and transmission of a beam of acoustic waves between an ultrasonic transducer and a remotely located body under examination by the beam.

SUMMARY OF THE INVENTION

The present invention provides efficient coupling and transmission of a beam of acoustic waves between an ultrasonic transducer and a remotely located body under examination by the beam.

The apparatus of the invention is preferably embodied as a catheter-type probe capable of imaging inside of a blood vessel, artery, or other tissue in a cavity of interest. Briefly, and in general terms, the present invention includes a housing having an interior arranged so that the ultrasonic transducer is disposed therein. A prism is acoustically coupled with the transducer and with an acoustic waveguide having a longitudinal dimension extending outwardly from the interior of the housing.

The acoustic prism is fixedly coupled with a proximate portion of the waveguide so as to provide efficient transmission of the beam of acoustic waves between the prism and the waveguide. Preferably, the waveguide includes a core and a cladding surrounding the core. In the preferred embodiment, the prism is fixedly coupled with the core of the waveguide for efficiently guiding the acoustic waves into the core of the waveguide. Accordingly, the beam of acoustic waves is transmitted from the transducer, through the prism, and along the longitudinal dimension of the waveguide, to a distal portion of the waveguide.

The distal portion of the waveguide is inserted into a remotely located cavity in the patient's body under examination. The distal portion of the waveguide emits the ultrasonic beam, scanning the tissue of interest. Accordingly, the invention provides efficient acoustic coupling between an ultrasonic transducer and a remotely located body under examination.

To provide for a simplified electrical connection to the transducer, it is preferred that the transducer is fixedly coupled with the housing. Preferably, the waveguide is rotated within the housing, so that the distal portion of the waveguide rotationally scans the tissue of interest while the housing remains substantially stationary. Since the prism is fixed to the waveguide, the prism rotates along with the waveguide and substantially reduces any fluctuations in the acoustic waves as the acoustic wave is transmitted from the prism into the waveguide. As the surface of the prism rotates with respect to the surface of the transducer, a fluid material disposed between the surface of the transducer and the surface of the prism advantageously provides acoustic coupling there between.

The transducer generates the beam of acoustic waves, which is incident on the prism and has a power level. The prism has a surface for reflecting the incident beam of acoustic waves to produce a reflected beam of acoustic waves having a power level. The power level of the incident beam of acoustic waves is adjusted based on feedback of the power level of the reflected beam of acoustic waves, so as to maintain the power level of the incident beam of acoustic waves at a desired level.

The beam of acoustic waves generated by the transducer includes longitudinal waves. In accordance with the preferred embodiment of the invention, the prism has an acoustic impedance and the waveguide has an acoustic impedance sufficiently different than that of the prism so as to substantially separate the longitudinal waves from any shear waves by acoustic refraction at the interface. Such separation is desired because shear waves travel at a lower velocity than the longitudinal waves and tend to obscure an acoustic image provided by longitudinal waves reflected by the body under examination. Preferably, the apparatus further includes an absorbing material coupled with a surface of the waveguide. The absorbing material is positioned at a location sufficiently near the refracted shear waves so as to substantially absorb the refracted shear waves. The location is sufficiently far from the refracted longitudinal waves so that the refracted longitudinal waves are substantially reflected within the waveguide, thereby providing for propagation of the refracted longitudinal waves along the longitudinal dimension or the waveguide.

Other aspects and advantages of the present invention will become apparent from the following detailed description, taken in conjunction with the accompanying drawings, illustrating by way of example the principles of the invention.

DETAILED DESCRIPTION OF PREFERRED EMBODIMENTS

Figure 1A:
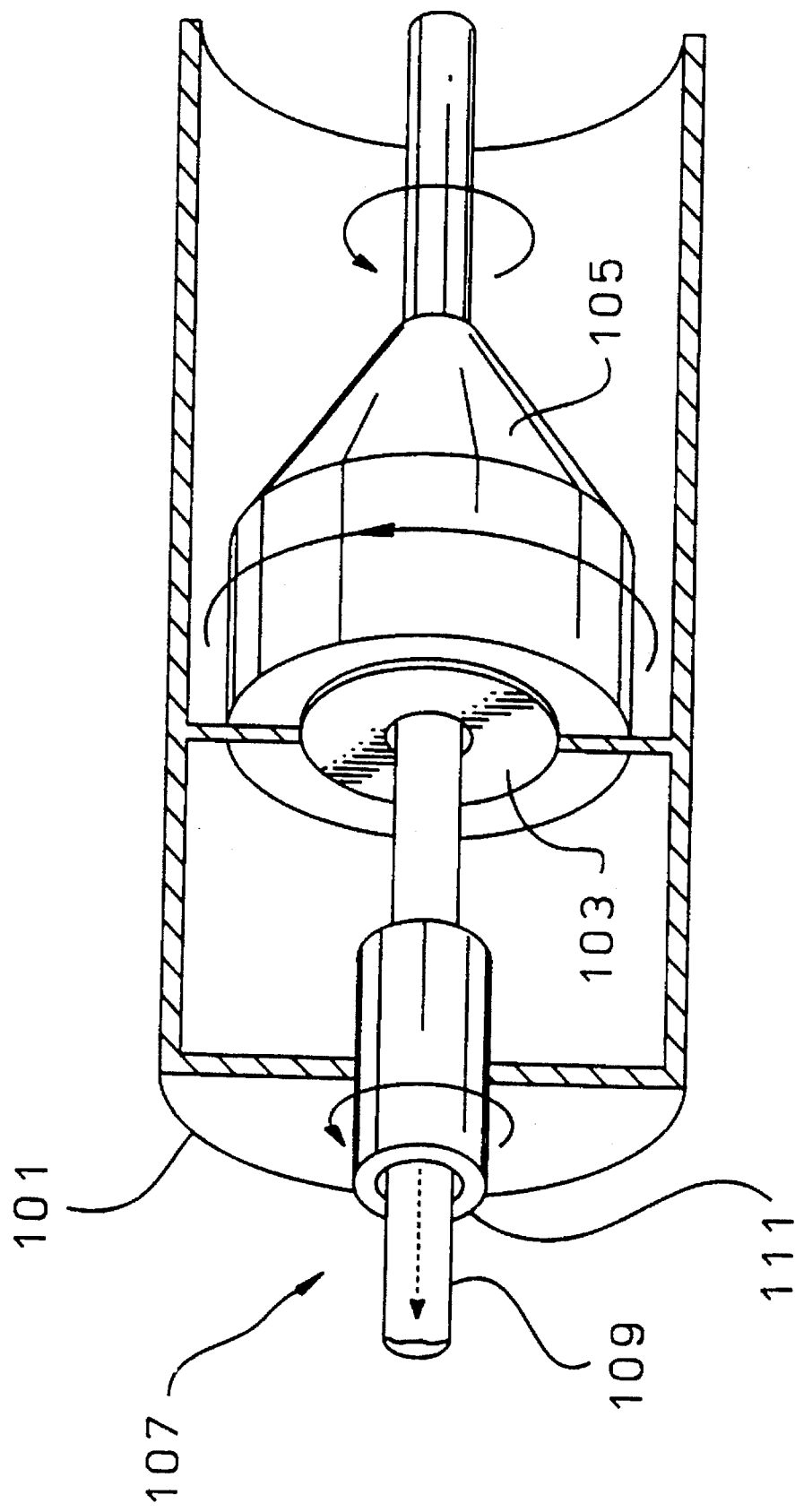
FIGS. 1A, 1B and 1C are views of the preferred embodiment of the invention.
Figure 1B:
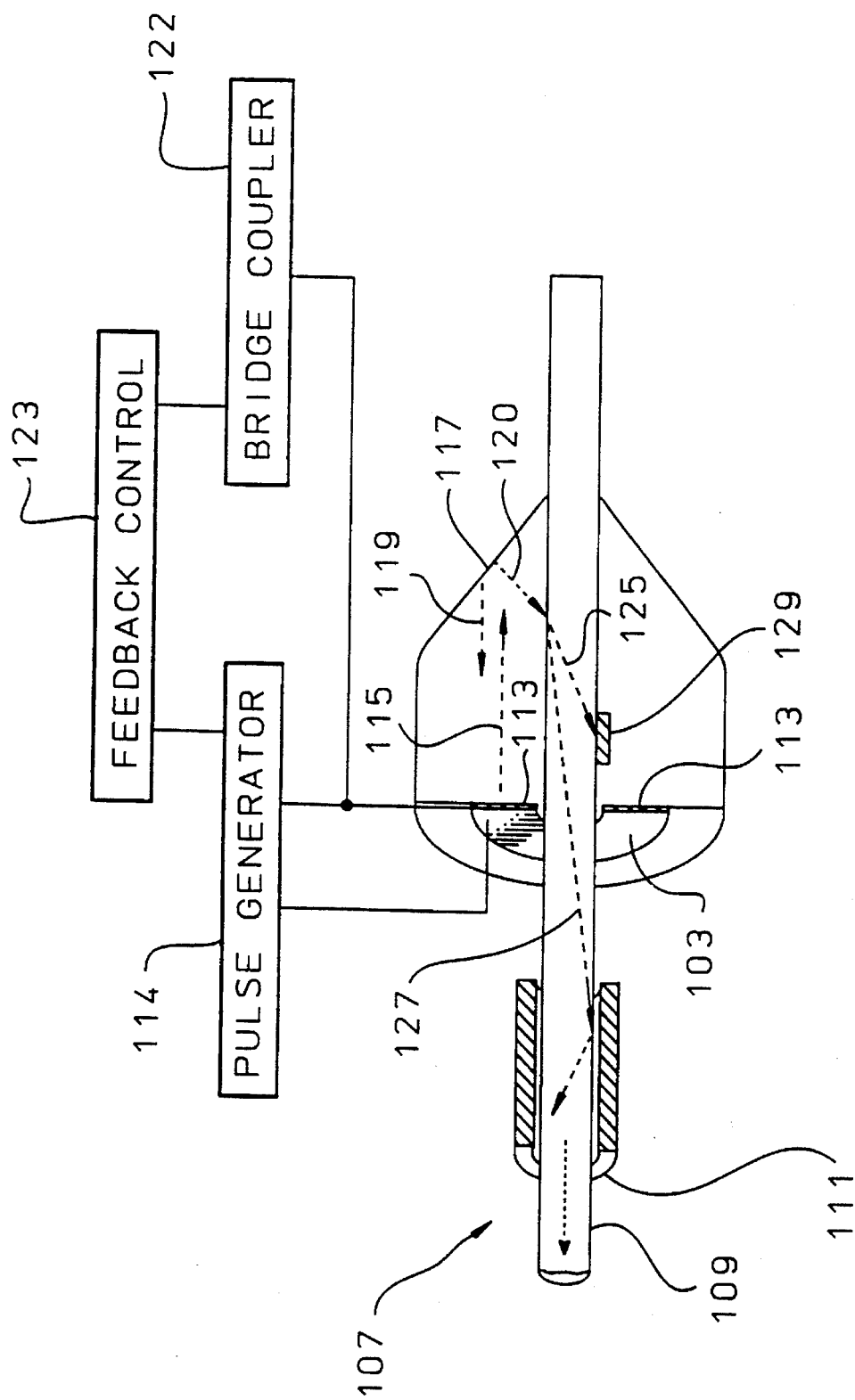
Figure 1C:
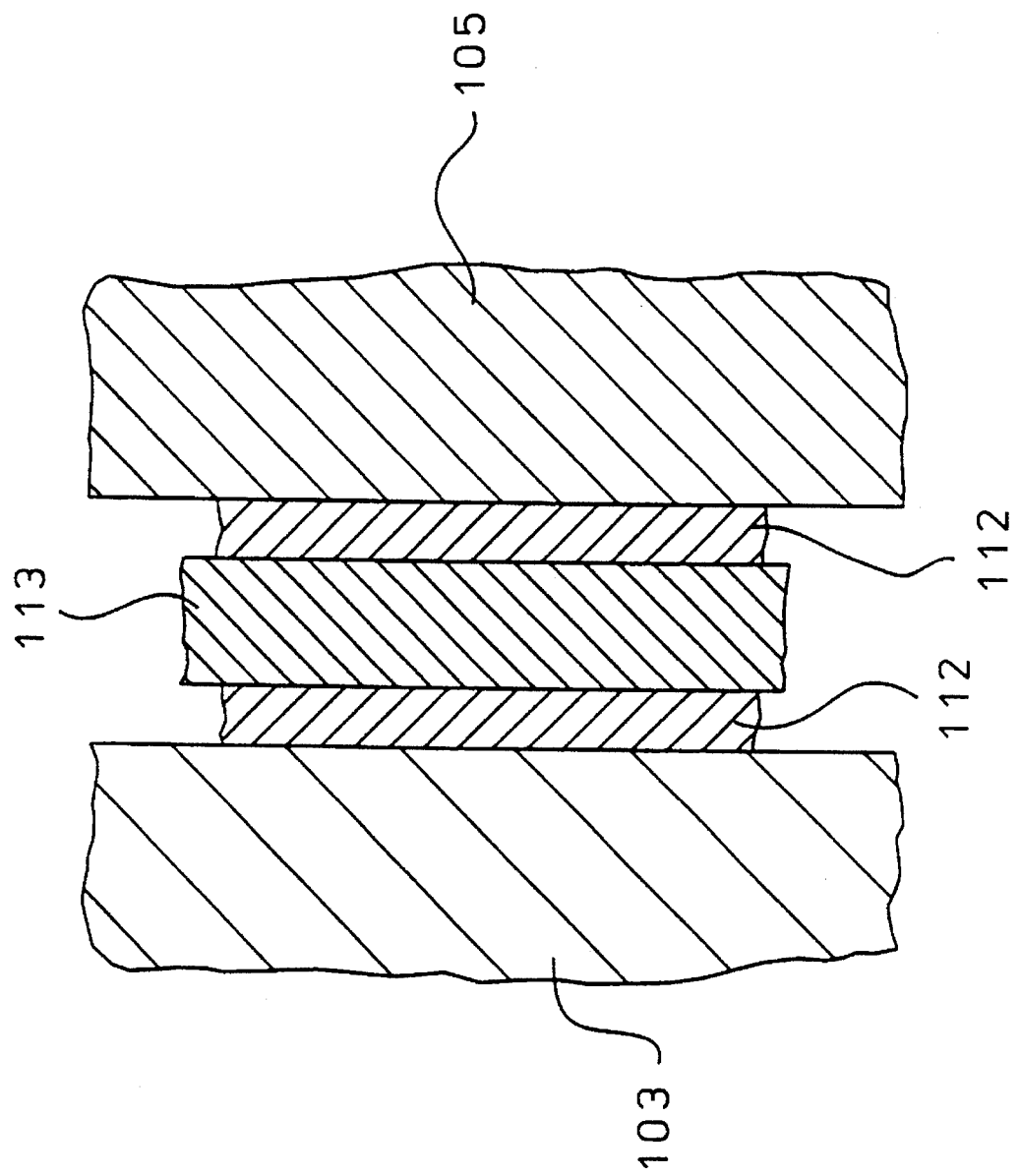

FIGS. 1A, 1B and 1C are views of the preferred embodiment of the invention. The apparatus of the invention is preferably embodied as a catheter-type probe capable of imaging inside of a blood vessel, artery, or other tissue in a cavity of interest. As shown in cut away view in FIG. 1A, the invention includes a housing 101. The housing has an interior arranged so that an ultrasonic transducer 103 is disposed therein. Preferably, the transducer includes an annulus of a suitable piezoelectric ceramic such as lead zirconate titanate. A high voltage pulse generator (not shown in FIG. 1A) is coupled with electrodes disposed on opposing surfaces of the annulus for electrically exciting the piezoelectric ceramic to generate acoustic waves. A thickness of the annulus is selected so that the acoustic waves have a desired frequency. Preferably, the transducer additionally includes a plurality of concentric piezoelectric ceramic annuli adapted for operation as a phased acoustic array, so as to provide a focussed beam of acoustic waves. A signal delay is coupled with each of the piezoelectric ceramic annuli for variably phasing a respective acoustic wave generated by each one of the piezoelectric ceramic annuli.

A prism 105 of a suitable material such as plexiglass is acoustically coupled with the transducer. An acoustic waveguide 107 having a longitudinal dimension extends outwardly from the interior of the housing. As shown in FIG. 1A, the acoustic prism is fixedly coupled with a proximate portion of the waveguide so as to provide efficient transmission of the beam of acoustic waves between the prism and the waveguide.

Preferably, the waveguide includes a core 109 of a suitable material, such as aluminum, and a cladding material 111 surrounding the core. The cladding material is selected so that a velocity of longitudinal acoustic waves in the cladding is greater than a velocity of longitudinal acoustic waves in the core material. It should be understood that while cladding surrounding an aluminum core is preferred, other suitable materials may be substituted therefor with beneficial results. For example, in an alternative embodiment the core comprises fused silica doped with germanium dioxide, while the cladding comprises un-doped silica.

In the preferred embodiment, the prism 105 is fixedly coupled with the core 109 of the waveguide for efficiently guiding the acoustic waves into the core of the waveguide. For example, the plexiglass is molded around the aluminum core as a resin, and the plexiglass resin is then hardened to be fixedly and acoustically coupled with the core of the waveguide. In operation of the invention, the beam of acoustic waves is transmitted from the transducer, through the prism, and into and along the longitudinal dimension of the waveguide, to a distal portion of the waveguide (not shown in FIGS. 1A and 1B).

To provide for a simplified electrical connection to electrodes of the transducer, it is preferred that the transducer 103 is fixedly coupled with the housing 101 as shown in FIG. 1A. The waveguide is rotated within the housing, manually or by using a motor coupled thereto, so that the distal portion of the waveguide rotationally scans the tissue of interest while the housing remains substantially stationary. Since the prism is fixed to the waveguide, the prism rotates along with the waveguide as shown in FIG. 1A and substantially reduces any fluctuations in the acoustic waves as the acoustic wave is transmitted from the prism into the waveguide. As the surface of the prism rotates with respect to the surface of the transducer, a fluid material, for example water, disposed between the surface of the transducer and the surface of the prism advantageously provides fluid acoustic coupling there between.

Furthermore, in the preferred embodiment, an annulus of a suitable material 113, for example a suitable teflon composite, is disposed adjacent to the fluid for substantially providing acoustic impedance matching between the transducer and the prism. For example, given that the piezoelectric ceramic of the preferred embodiment of the transducer has an acoustic impedance of thirty Megarayls, and that the plexiglass of the preferred embodiment of the prism has an acoustic impedance of three and a half Megarayls, the preferred teflon composite has an acoustic impedance that substantially provides the desired impedance matching.

FIG. 1B is a partial schematic diagram showing a cross-section view of the transducer 103, prism 105, and waveguide 107, which reveals the fluid material 112 disposed between the transducer and the prism. FIG. 1C is a detailed cut away view further revealing the fluid material 112 as well as the impedance matching material 113 disposed between the transducer 103 and the prism 105. For the sake of simplicity, the housing is not shown in FIGS. 1B and 1C.

Relatively speaking, a surface area of an acoustic interface between the transducer and the prism of the preferred embodiment is large, while a surface area of an acoustic interface between the prism and the waveguide of the preferred embodiment is small. In general, the large surface area provides enhanced acoustic transmission efficiency, while the small surface area provides only limited acoustic transmission efficiency. Furthermore, the fixed coupling provides enhanced acoustic transmission efficiency, while fluid coupling provides only limited acoustic transmission efficiency. Therefore, in accordance with the principles of the invention, the enhanced acoustic transmission efficiency provided by the fixed coupling between the prism and the waveguide substantially offsets the limited acoustic transmission efficiency provided by the relatively small surface area of the acoustic interface between the prism and the waveguide. Similarly, in accordance with the principles of the invention, the enhanced acoustic transmission provided by the relatively large surface area of the acoustic interface between the transducer and the prism substantially offsets the limited acoustic transmission provided by the fluid coupling between the transducer and the prism.

As shown in FIG. 1B, the high voltage pulse generator 114 electrically excites the transducer to generate the beam of acoustic waves 115, which is incident on the prism and has a power level. Of course, acoustic waves are invisible. However the beam generated by the transducer is representatively illustrated in FIG. 1B as a dashed line. The prism has a surface 117 for reflecting the incident beam of acoustic waves to produce a weakly reflected beam of acoustic waves 119 having a power level, and further to produce a strongly reflected beam of acoustic waves 120 that is guided into the waveguide.

A sensor, preferably a bridge coupler, 122 is coupled with the transducer so as to electrically sense the weakly reflected beam of acoustic waves 119. A feedback control circuit 123 is coupled with the pulse generator and sensor for adjusting the power level of the incident beam of acoustic waves 115 so as to maintain the power level of the incident beam of acoustic waves at a desired level, based upon feedback of the power level of the weakly reflected beam of acoustic waves.

The beam of acoustic waves generated by the transducer includes longitudinal waves. It is theorized that the longitudinal waves incident on the interface between the prism and the waveguide are mode converted into both shear waves 125 and longitudinal waves 127. In accordance with the preferred embodiment of the invention, the prism has an acoustic impedance and the waveguide has an acoustic impedance sufficiently different than that of the prism so as to substantially separate the longitudinal waves 127 from any shear waves 125 by acoustic refraction at the interface. Furthermore, it is preferred that the waveguide has a higher acoustic impedance than the prism, so that the longitudinal waves 127 are guided along the longitudinal dimension of the waveguide at an advantageous initial angle.

For example, the plexiglass of the prism of the preferred embodiment has an acoustic impedance of three and a half Megarayls. The aluminum of the preferred embodiment of the waveguide has an acoustic impedance of seventeen Megarayls, which is sufficiently different from that of the prism for substantially separating the longitudinal waves 127 from the shear waves 125 as shown in FIG. 1B. For example using Snell's law, given these acoustic impedances and given that the surface of the prism 117 is oriented so the strongly reflected beam of acoustic waves 120 is incident with a normal of the interface between the prism and waveguide at a twenty four degrees, then the shear waves 125 will be separated form the longitudinal waves 127 by an angle of approximately forth five degrees. Such separation is desired because shear waves travel at a lower velocity than the longitudinal waves and tend to obscure an acoustic image provided by longitudinal waves reflected by the body under examination by the probe. In this example, the longitudinal waves 127 are guided along the longitudinal dimension of the waveguide at an advantageous initial angle of seventy two degrees with respect to the normal of the interface.

The preferred embodiment further includes an acoustic absorbing material 129, for example an epoxy compound, coupled with a surface of the waveguide, as revealed by the cross sectional view of the prism and waveguide shown in FIG. 1B. The absorbing material is positioned at a location sufficiently near the refracted shear waves 125 so as to substantially absorb the refracted shear waves 125. The location is sufficiently far from the refracted longitudinal waves 127 so that the refracted longitudinal waves are substantially reflected within the waveguide as shown in FIG. 1B, thereby providing for propagation of the refracted longitudinal waves along the longitudinal dimension or the waveguide.

The present invention provides efficient coupling and transmission of a beam of acoustic waves between an ultrasonic transducer and a remotely located body under examination by the beam. Although specific embodiments of the invention have been described and illustrated, the invention is not to be limited to the specific forms or arrangements so described and illustrated, and various modifications and changes can be made without departing from the scope and spirit of the invention. For example, in an alternative embodiment of the invention, the waveguide and the prism are made from the same material, so as to substantially avoid mode conversion of the longitudinal waves into both longitudinal waves and shear waves. Within the scope of the appended claims, therefore, the invention may be practiced otherwise than as specifically described and illustrated.

What is claimed is:

1. An apparatus comprising:

a housing having an interior;

an ultrasonic transducer for generating a beam of acoustic waves, which is disposed within the housing;

a prism acoustically coupled with the transducer; and an acoustic waveguide extending outwardly from the interior of the housing, the acoustic prism being fixedly coupled with the waveguide so as to provide efficient transmission of the acoustic waves between the prism and the waveguide.

2. An apparatus as in claim 1 wherein:

the waveguide includes a core and a cladding surrounding the core; and the prism is acoustically coupled with the core of the waveguide for guiding the acoustic wave into the core of the waveguide.

3. An apparatus as in claim 2 wherein the prism is fixedly coupled with the core of the waveguide.

4. An apparatus as in claim 1 further comprising a means for rotating the waveguide within the housing.

5. An apparatus as in claim 4 wherein the prism is fixed to the waveguide, so that the prism rotates along with the waveguide.

6. An apparatus as in claim 5 wherein the transducer is fixedly coupled with the housing, so that the housing and transducer remain substantially stationary as the prism rotates along with the waveguide.

7. An apparatus as in claim 1 wherein:

the transducer has an acoustic impedance;

the prism has an acoustic impedance different than that of the transducer; and the apparatus further comprises an impedance matching material coupled with the transducer and the prism for providing an acoustic impedance match between the transducer and the prism.

8. An apparatus as in claim 1 further comprising:

a pulse generator coupled with the transducer for generating a beam of acoustic waves that is incident on the prism and that has a power level, wherein the prism has a surface for reflecting the incident acoustic wave to produce a reflected acoustic wave having a power level; and a sensor coupled with the prism for sensing the power level of the reflected wave.

9. An apparatus as in claim 8 further comprising a feedback circuit coupled with the pulse generator for adjusting the power level of the incident wave based on the power level of the reflected wave.

10. An apparatus as in claim 1 wherein the transducer includes a piezoelectric ceramic annulus.

11. An apparatus comprising:

an ultrasonic transducer for generating a beam of acoustic waves including longitudinal waves;

a prism having an acoustic impedance coupled with the transducer; and a waveguide coupled with the prism at an acoustic interface, the waveguide having an acoustic impedance sufficiently different than that of the prism so as to substantially separate the longitudinal waves from any shear waves by acoustic refraction at the interface.

12. An apparatus as in claim 11 wherein:

the waveguide has a surface and a longitudinal dimension; and the apparatus further comprises an absorbing material coupled with the surface of the waveguide and positioned at a location, which is sufficiently near the refracted shear waves so as to substantially absorb the refracted shear waves, and which is sufficiently far from the refracted longitudinal waves so that the refracted longitudinal waves are substantially reflected within the waveguide, thereby providing for propagation of the refracted longitudinal waves along the longitudinal dimension or the waveguide.

* * * * *